(12) United States Patent
Kinne

(10) Patent No.: US 6,590,375 B1
(45) Date of Patent: Jul. 8, 2003

(54) DEVICE AND METHOD FOR DETECTION AND/OR INSPECTION OF CONDUCTIVE PARTICLES USING HIGH-VOLTAGE FIELD

(75) Inventor: William E. Kinne, Edgewood, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/974,123

(22) Filed: Oct. 9, 2001

Related U.S. Application Data

(62) Division of application No. 09/415,835, filed on Oct. 12, 1999, now Pat. No. 6,323,633.

(51) Int. Cl.[7] .................. G01N 27/00; G01N 27/62; G01R 31/16; H01H 9/50
(52) U.S. Cl. .................. 324/71.1; 324/464; 324/515; 324/536
(58) Field of Search .................. 324/71.1, 71.4, 324/459, 464, 536, 457, 458, 558, 448, 449, 515; 73/865.5, 61.66; 422/186.04; 204/164; 96/27; 250/382

(56) References Cited

U.S. PATENT DOCUMENTS

| | | | | |
|---|---|---|---|---|
| 3,580,075 A | * | 5/1971 | Steinberg | 374/118 |
| 3,614,516 A | * | 10/1971 | Phillips | 315/3.5 |
| 4,090,308 A | * | 5/1978 | Stuck | 324/464 |
| 4,165,482 A | * | 8/1979 | Gale | 324/523 |
| 4,435,681 A | * | 3/1984 | Masuda et al. | 324/459 |
| 4,767,995 A | * | 8/1988 | Berry, Jr. | 324/447 |
| 5,194,815 A | * | 3/1993 | Maeno | 324/501 |
| 5,198,773 A | * | 3/1993 | Latta | 324/464 |
| 5,276,401 A | * | 1/1994 | Soma et al. | 324/551 |
| 5,318,861 A | * | 6/1994 | Harats et al. | 429/21 |
| 5,439,571 A | * | 8/1995 | Sammons et al. | 204/549 |
| 5,617,033 A | * | 4/1997 | Kashioka et al. | 324/539 |
| 6,094,045 A | * | 7/2000 | Zoellick | 324/115 |

* cited by examiner

Primary Examiner—Anjan K. Deb
(74) Attorney, Agent, or Firm—Ulysses John Biffoni

(57) ABSTRACT

Particles in a fluid cause an arc at a certain electric field whose value depends on the nature of the particles (size, composition, and the like). By applying an electric field across the fluid and determining the value of the electric field at which the arc occurs, the nature of the particles can be determined. For example, if their composition is known, their size can be determined, and vice versa. The device for carrying out such testing has a first electrode with an interior opening and a second electrode having a pin through the interior opening to define a passageway for the fluid. The electric field is varied, either by varying a voltage applied between the electrodes or by forming the passageway to be tapered. Multiple such passageways can be provided, as by forming the first electrode from honeycomb-expanded metal, thus reducing pressure drop, energy consumption without decreasing sensitivity to low concentrations.

7 Claims, 4 Drawing Sheets

DEVICE AND METHOD FOR DETECTION AND/OR INSPECTION OF CONDUCTIVE PARTICLES USING HIGH-VOLTAGE FIELD

This application is a division of application Ser. No. 09/415,835, filed on Oct. 12, 1999, now U.S. Pat. No. 6,323,633.

GOVERNMENTAL INTEREST

The invention described herein may be manufactured, used and licensed by or for the U.S. Government.

1. Field of the Invention

The invention is directed to an apparatus and method for detecting low concentrations of a smoke having a small particle size (e.g., 10 microns).

2. Description of Related Art

There is a need in the art to detect smoke having low concentrations and a small particle size (e.g., 10 μparticles of carbon or brass). Conventional detection of such smoke has relied on optical detection using visible, infrared, or ultraviolet light. However, such optical detection is dependent on the particles' ability to scatter, absorb, or forward scatter light and have limited performance in extremely low concentrations of smoke.

Co-pending application Ser. No. 09/400,146, filed Sep. 12,1999, entitled "Device and Method for Inspection and Detection of a Material by Observing a High-Voltage Waveform Produced by that material", teaches detecting low impedance fibers by providing a high voltage between two brass screens and observing an arc when a fiber bridges the gap between the screens. However, this technique is not well suited to detecting small particles, as the gap between the screens is far too large. Flat-plate designs used in corona-discharge systems for spectroscopy are similarly unsatisfactory.

SUMMARY OF THE INVENTION

It is an object of the invention to detect the presence of smoke (e.g., particles of carbon or brass) in a fluid, particularly in air.

It is another object of the invention to detect the presence of smoke in a large volume of air.

It is a further object of the invention to detect the presence of smoke with a reduced lag time while detecting the smoke in an enclosure.

It is a further object of the invention to detect the presence of smoke in a device with a small pressure drop so as to conserve power and reduce noise.

To achieve these and other objects, the present invention is directed to a detector for detecting particles in a fluid, the detector comprising: a voltage supply for supplying an adjustable voltage; a first electrode having at least one interior opening extending through the first electrode; and a second electrode comprising at least one pin extending through the at least one interior opening to define at least one passageway for the fluid; the first electrode and the second electrode being connected to the voltage supply so that the adjustable voltage is applied between the first electrode and the second electrode. The present invention is further directed to a detector for detecting particles in a fluid, the detector comprising: a voltage supply for supplying a voltage; a first electrode having an interior opening extending through the first electrode; and a second electrode comprising a pin extending through the interior opening to define a passageway for the fluid; the first electrode and the second electrode being connected to the voltage supply so that the voltage is applied between the first electrode and the second electrode to define an electric field between the first electrode and the second electrode; and at least one of the interior opening and the pin being shaped so that the passageway is tapered and the electric field varies along the length a method of detecting particles in a fluid, the method comprising: (a) providing a detector comprising (i) a voltage supply for supplying a voltage, (ii) a first electrode having at least one interior opening extending through the first electrode, and (iii) a second electrode comprising at least one pin extending through the at least one interior opening to define at least one passageway for the fluid, the first electrode and the second electrode being connected to the voltage supply so that the voltage is applied between the first electrode and the second electrode to produce an electric field between the first electrode and the second electrode; (b) introducing the fluid into the passageway; (c) applying the voltage from the voltage supply to the first electrode and the second electrode; (d) varying the electric field; (e) determining a value of the electric field at which an arc occurs in the fluid; and (f) detecting the particles in accordance with the value of the electric field determined in step (e).

The invention works on the principle that the discharge threshold, which is the potential difference required for a breakdown of an electrical field (E field) to produce an arc, is dependent on the conductivity of the sum of the impedances of the media between the opposing electrodes used to apply the potential difference and on the distance between the electrodes. The conductivity is influenced by the base medium (such as air), the presence of foreign particles in the base medium (such as carbon particles in smoke), and the size and composition of the particles. If the base medium is uniform (as is the case with air and water), it is the particles which cause the change in the discharge threshold. Since the effects of the particles are determined both by their size and by their conductivity, particles in a stream can be analyzed. If the material is contaminated, e.g., with water, the conductivity changes, and so does the threshold.

A design featuring a cylinder with a rod or pin in the center, both of which function as electrodes, and a design featuring a honeycomb arrangement of such cylinders and rods or pins allow a large cross-sectional area for air flow and thus are relatively unobtrusive to the fluid flow while minimizing the distance between the electrodes. Thus, sensitivity is improved, while high flow rates and low pressure drop are maintained.

The discharge threshold also depends on the particle size. If it is important to detect particle size as well, the E field can be set so as to detect particles above or below a cutoff size by determining whether the arc occurs. The E field can be varied during such detection, and the value at which the arc starts or stops allows a determination of the particle size.

The limit setting of the E field is dependent on the particle size and conductivity. In a stream of unknown particles, this dependence allows a level of filtering particle types by varying the E field.

A preferred embodiment of the invention uses highly charged conductive probes (electrodes) spaced apart to form an E field and senses the voltage required to cause an arc. The voltage between the electrodes, and with it the E field, can be increased or decreased, and knowledge of the voltage at which arcing occurs allows a determination of the content (chemical composition of the particles) if the particle sizes and concentrations are known. In the case of particles having a known chemical composition, the size or concentration of the particles can be determined. These determinations are possible because particles of the same size and different compositions are at different voltages, as do particles of different sizes and the same composition. An experiment was conducted with cigarette smoke, in which the difference between inhaled and uninhaled smoke could be seen.

The device and method according to the present invention are highly sensitive to all kinds of conductive particles and is especially valuable for small particles. The present invention is not dependent on the particles' ability to scatter, absorb, or forward scatter light in the IR, visible, or UV range.

Conductive particles have uses in both governmental and commercial areas. Besides detection and identification of obscurants in military applications, the invention can be used to detect contaminants in water or another fluid.

While it is contemplated that the invention will be used with an air flow, any fluid can be used.

BRIEF DESCRIPTION OF THE DRAWINGS

Preferred embodiments of the present invention will be set forth in detail with reference to the drawings, in which.

DETAILED DESCRIPTION OF THE PREFERRED EMBODIMENTS

Figure 1:
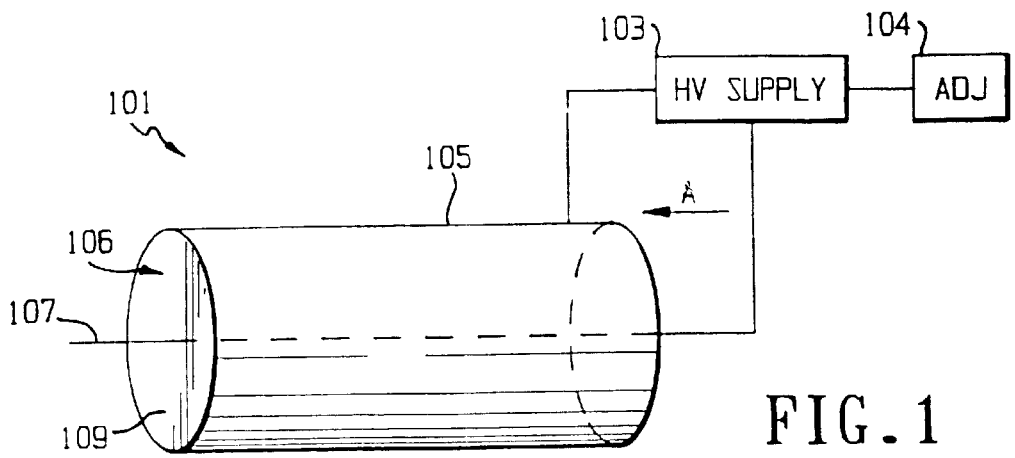
FIG. 1 shows a side schematic view of a detector according to a first embodiment of the present invention.
Figure 2:
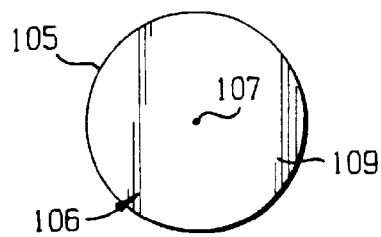
FIG. 2 shows a head-on view of the electrodes in the detector of FIG. 1.

FIG. 1 shows a side schematic view of a detector according to a first embodiment of the present invention. In detector 101, high-voltage (HV) supply 103, which can be any suitable HV supply and which can be adjusted through manual or automatic adjustment control 104, supplies a potential difference to two electrodes, namely, cylinder 105 having interior opening 106 and pin 107 disposed in interior opening 106 of cylinder 105. Pin 107 is preferably disposed in the center of cylinder 105, as shown in a head-on view in FIG. 2. Cylinder 105 and pin 107 define passageway 109 between them, formed in part of interior opening 106, to accommodate an air flow, which can be in the direction shown by arrow A or in the opposite direction.

Figure 3:
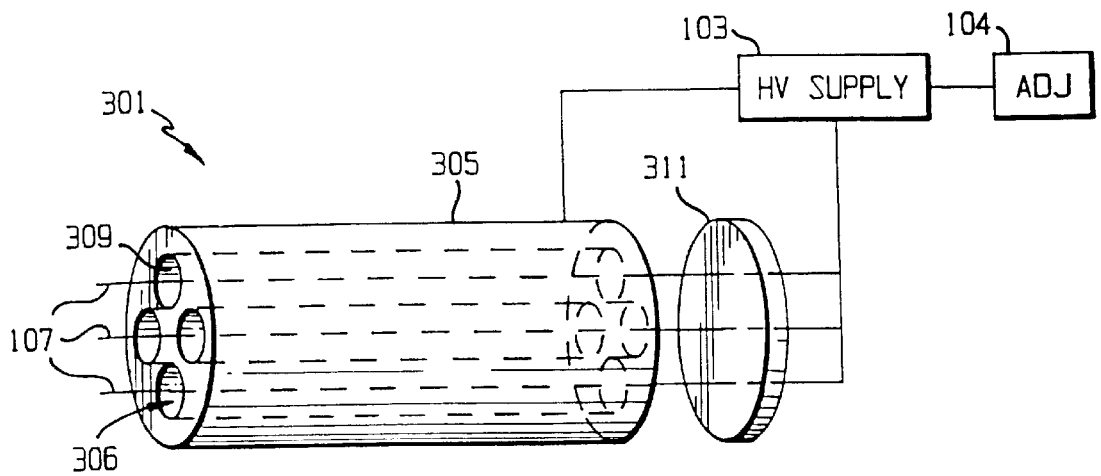
FIG. 3 shows a side schematic view of a detector according to a modification of the first embodiment of the present invention.

FIG. 3 shows a side schematic view of a modified version of detector 101 of FIG. 1. Detector 301 of FIG. 3 differs from detector 101 of FIG. 1 in that cylinder 105 is replaced with electrode 305 having multiple interior openings 306 therein and that multiple pins 107 are provided, each in one of multiple interior openings 306. Each combination of a pin 107 and an interior opening 306 defines a passageway 309 for air flow. The arrangement of pins 107, interior openings 306 and passageways 309 in electrode 305 is shown in a head-on view in FIG. 4. HV supply is connected to electrode 305 and to each of pins 107.

Figure 4:
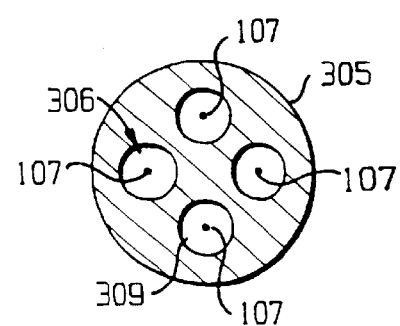
FIG. 4 shows a head-on view of the electrodes in the detector of FIG. 3.

The configuration shown in FIGS. 3 and 4 offers advantages in terms of ease of alignment, a small gap between electrode 305 and each of pins 107, and the availability of materials. Such a configuration allows many close-gapped electrodes with tight tolerance in spacing to be contained in a small cross section and still to provide a large open area, reducing pressure drop at high fluid flow and thus reducing power consumption. Also, a lower linear velocity of fluid flow can be used while maintaining a suitable flow in terms of volume per unit time.

Electrode 305 can be formed from honeycomb-expanded metal. Such honeycomb-expanded metals are known, and available materials offer suitable conductivity and dimensional. stability. Alternatively, electrode 305 can be formed from multiple cylinders, generally like cylinder 105, held together in a suitable manner.

Pins 107 are brass brads. In modified detector 301, pins 107 are mounted on precision-drilled brass plate 311 with hole dimensions providing a force fit. This arrangement provides a conductive, mechanically stable support for extremely close air gaps between pins 107 and electrode 305.

Figure 5:
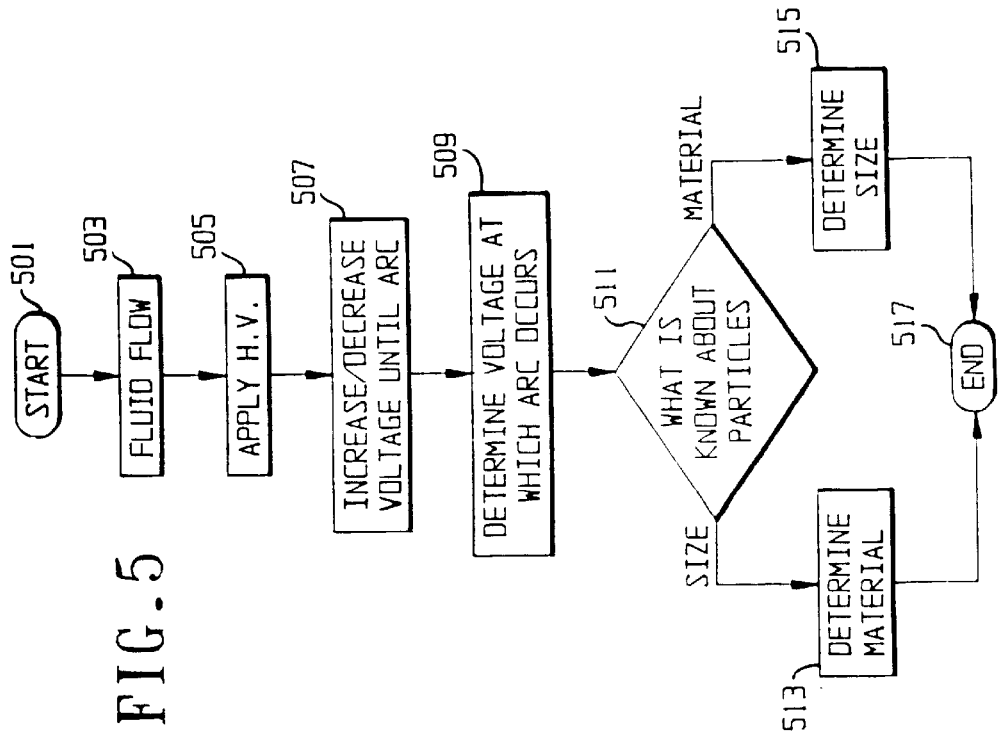
FIG. 5 shows a flow chart of operational steps implemented with the detector of FIG. 1 or FIG. 3.

Detector 101 and detector 301 can be used to implement the series of operational steps shown in the flow chart of FIG. 5. These steps can be performed either manually or automatically, as by any suitably programmed computer.

The operation starts in step 501. In step 503, a fluid flow is started in passageway 109 or passageways 309, either by providing a blower or by exposing detector 101 or 301 to wind or to fluid flow. In step 505, the high voltage is applied from HV supply 103. In step 507, the voltage applied from HV supply 103 is increased or decreased by controlling HV supply 103 through adjustment control 104, thus also increasing or decreasing the E field, until an arc occurs. In step 509, the voltage at which arc occurs is determined.

Steps 511–515 involve determining an unknown characteristic of the particles from the voltage and another known characteristic. For example, it is determined in step 511 whether the particles are of a known size or of a known material. If they are of a known size, the material is determined in step 513. On the other hand, if they are of a known material, the size is determined in step 515. Other characteristics, such as concentration, can be detected if enough information about the particles is already known. The range of characteristics that can be detected is especially broad if particle size can be determined in another way, e.g., optically. Either way, the operation ends in step 517.

The first embodiment of the invention, as disclosed in FIGS. 1–5 and the description thereof set forth above, has been experimentally verified to work with carbon smoke particles, brass smoke particles and cigarette smoke. It was experimentally verified that a single particle of smoke could be detected with a sufficiently high E field and that inhaled cigarette smoke could be distinguished from uninhaled cigarette smoke.

In the first embodiment, the E field is varied by controlling the HV supply. A second embodiment will now be set forth in detail, in which the E field is varied by displacement along the length of the detector.

Figure 6:
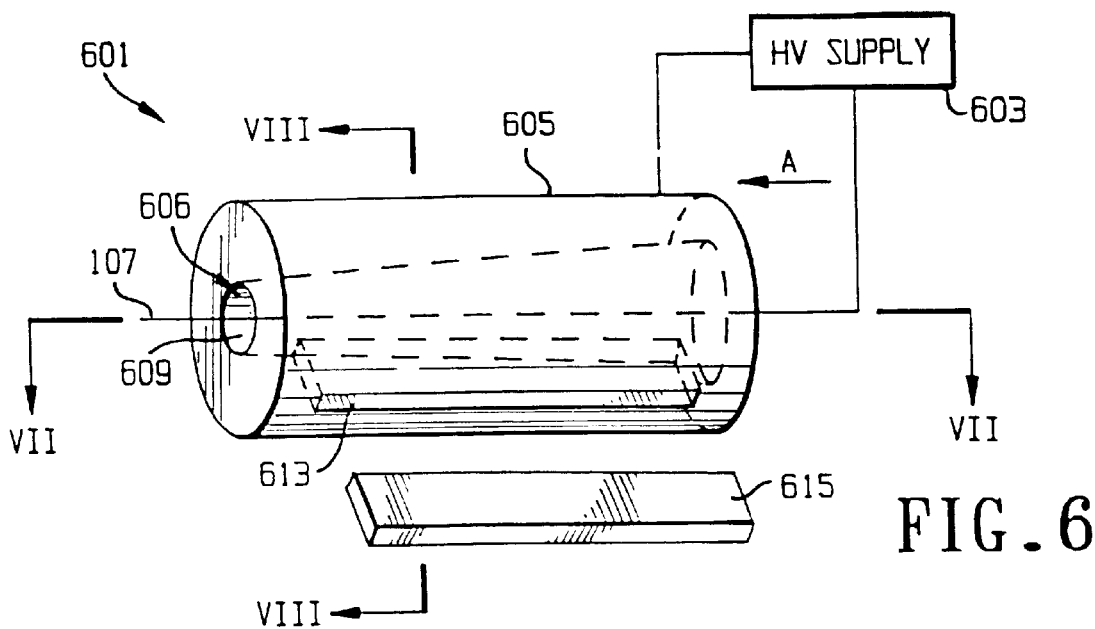
FIG. 6 shows a side schematic view of a detector according to a second embodiment of the present invention.
Figure 7:
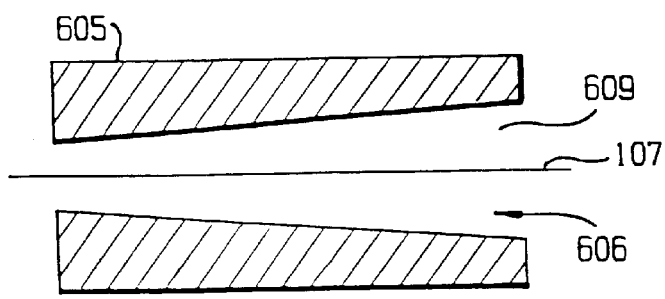
FIGS. 7 and 8 show cross-sectional views of the detector of FIG. 6.
Figure 8:
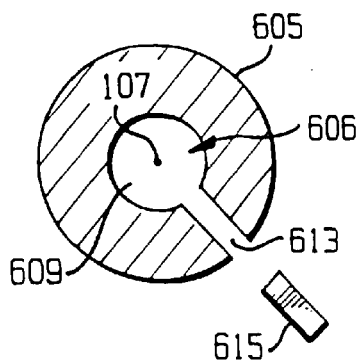

FIG. 6 shows a side schematic view of a detector according to the second embodiment. FIGS. 7 and 8 are cross-sectional views taken along arrows VII—VII and VIII—VIII, respectively.

As shown in FIGS. 6–8, detector 601 includes HV supply 603 which is not required to be adjustable. Electrode 605 has tapered hole (interior opening) 606 therethrough to provide tapered passageway 609 for fluid flow, preferably in the direction indicated by arrow A. Slot 613 extends from the outermost surface of electrode 605 to passageway 609 to allow observation of the location at which arcing occurs. Pin 107 is disposed in tapered hole 606 to define passageway 609, preferably in the center of electrode 605. Arcing in passageway 609 can be observed through slot 613, either directly by a person or with photocell array 615.

Because of tapered passageway 609, the distance between electrode 605 and pin 107 varies along the length of the detector, and with it the E field. Thus, for a constant E field, the discharge threshold occurs at a specific location along passageway 609. Observation of this location through slot 613 allows determination of the E field and thus of the desired characteristic of the particles.

Figure 9:
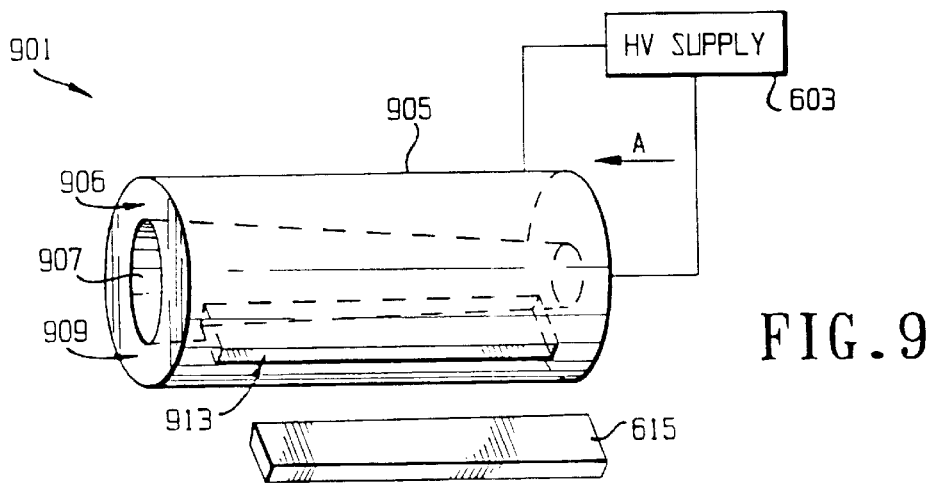
FIG. 9 shows a side schematic view of a detector according to a modification of the second embodiment of the present invention.

FIG. 9 shows a side schematic view of a modified version of detector 601 of FIG. 6. Detector 901 of FIG. 9 includes HV supply 603 and photodetector array 615 like those of detector 601 of FIG. 6. However, detector 901 includes cylinder 905, whose interior opening 906 is not tapered, and tapered pin 907 to provide passageway 909 with a position-varying gap between cylinder 905 and tapered pin 907. Cylinder 905 can be like cylinder 105 of detector 101 of FIG. 1, except for slot 913 to allow observation of the arc.

The location of the arc can alternatively be detected in accordance with a distributed-ground technique. This technique relies on the fact that at the location of an arc, current flow markedly increases. Detection of the increased current flow allows detection of the location of the arc. Both the interior opening and the pin could be tapered.

Figure 10:
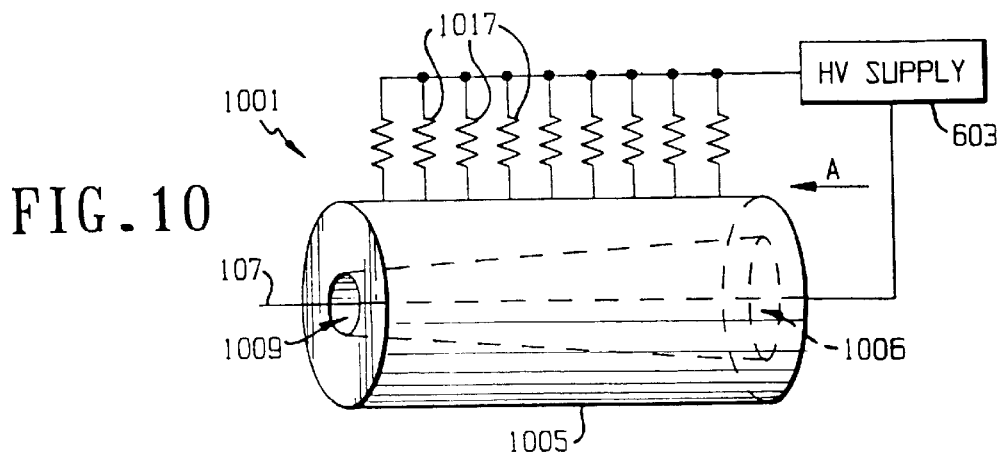
FIG. 10 shows a side schematic view of a detector according to another modification of the second embodiment.

FIG. 10 shows a side schematic view of detector 1001, which is similar to detector 601 of FIG. 6 in having HV supply 603 and pin 107. However, electrode 1005 differs from electrode 605 in not having slot 613. Interior opening 1006 and tapered passageway 1009 are thus like interior opening 606 and tapered passageway 609, except without any interruption for a slot.

Detector 1001 differs further from detector 601 in that HV supply 603 and electrode 1005 are connected through an array of detection resistors 1017 in parallel. Detection resistors 1017 change some physical property when current passing through them goes over a threshold. The location of the arc can thus be determined in accordance with this changed physical property. Alternatively, conventional resistors could be used, and the current flow could be detected across each of the conventional resistors.

Figure 11:
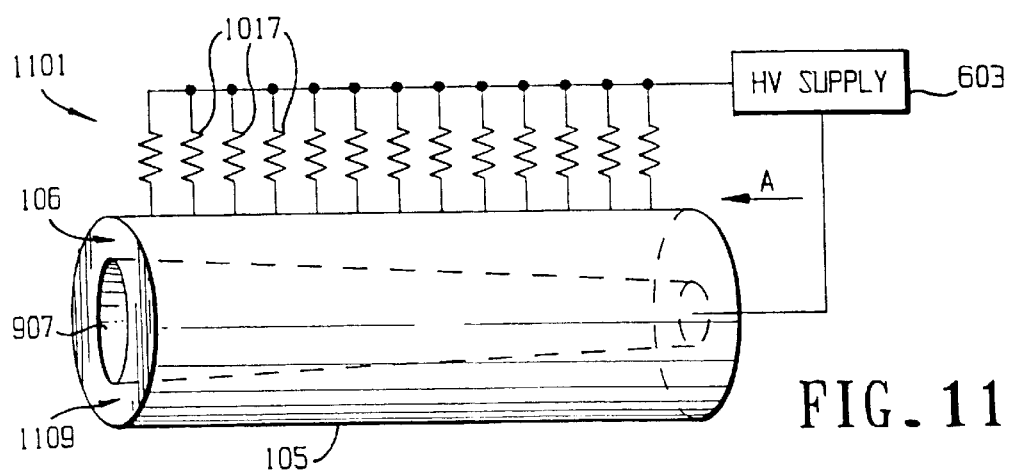
FIG. 11 shows a side schematic view of a detector according to still another modification of the second embodiment.

The modifications shown in FIGS. 9 and 10 can be modified to form detector 1101 of FIG. 11. Detector 1101 combines detection resistors 1017 of detector 1001 with tapered pin 907 of detector 901 and cylinder 105, with no slot and with non-tapered interior opening 106, of detector 101. The combination of cylinder 105 and tapered pin 907 forms passageway 1109, which is like passageway 909 except for the absence of a slot. Again, both the pin and the is interior opening could be tapered.

Any of detectors 601, 901, 1001, and 1101 can be modified to have multiple passageways, as does detector 301.

Figure 12:
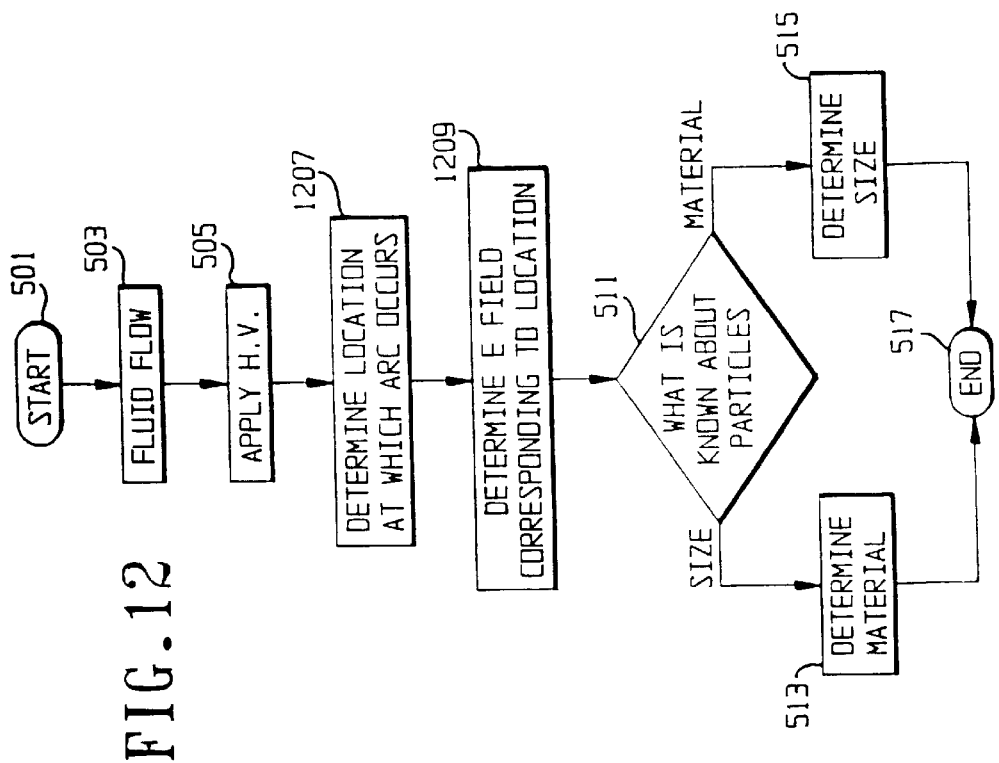
FIG. 12 shows a flow chart of operational steps implemented with the detector of FIG. 6, FIG. 9, FIG. 10, or FIG. 11.

The detectors of FIGS. 6–11 can be used to implement the series of operational steps shown in the flow chart of FIG. 12. The operational steps of FIG. 12 are the same as those of FIG. 5, except that steps 507 and 509 are replaced with step 1207 of determining a location at which the arc occurs (either by photodetector array 615 or by detection resistors 1017) and step 1209 of determining an electric field corresponding to that location.

While two preferred embodiments of the invention have been described in detail, each with variations, those skilled in the art who have reviewed this disclosure will readily appreciate that other embodiments can be described within the scope of the invention. For example, modifications disclosed together can be used separately, while modifications disclosed separately can be combined. Also, any conventional analytical hardware, software, or techniques can be incorporated into setups according to the invention. Any disclosed process can be automated. The data collected can be combined with electron microscope pictures, manufacturing information, low-voltage measurements, or any other information useful in analysis of the material. Materials and numbers of components disclosed are illustrative rather than limiting.

I claim:

1. A detector for detecting particles in a fluid, the detector comprising:

a voltage supply for supplying a voltage;

a first electrode having an interior opening extending through the first electrode; and a second electrode comprising a pin extending through the interior opening to define a passageway for the fluid;

the first electrode and the second electrode being connected to the voltage supply so that the voltage is applied between the first electrode and the second electrode to define an electric field between the first electrode and the second electrode; and at least one of the interior opening and the pin being shaped so that the passageway is tapered and the electric field varies along a length of the pin.

2. A detector as in claim 1, wherein the interior opening is tapered.

3. A detector as in claim 1, wherein the pin is tapered.

4. A detector as in claim 1, wherein the first electrode has a slot extending to the interior opening to allow observation of the passageway.

5. A detector as in claim 4, further comprising a photodetector array adjacent to the slot to allow the observation of the passageway by the photodetector array.

6. A detector as in claim 1, wherein the voltage supply is connected to the first electrode through an array of resistors which are disposed in parallel.

7. A detector as in claim 6, wherein each of the resistors in the array is a detection resistor which changes a physical property in accordance with a flow of current in said detection resistor.

* * * * *